United States Patent [19]

Rocco et al.

[11] Patent Number: 5,837,714
[45] Date of Patent: Nov. 17, 1998

[54] SOLID PHARMACEUTICAL DISPERSIONS

[75] Inventors: William Rocco, Reading; Sharon Laughlin, Phoenixville, both of Pa.

[73] Assignee: Sanofi, Paris Cedex, France

[21] Appl. No.: 813,946

[22] Filed: Mar. 3, 1997

[51] Int. Cl.$^6$ .......................... A61K 31/47; A61K 31/19; A61K 31/08; A61K 31/045
[52] U.S. Cl. .......................... 514/313; 514/569; 514/723; 514/738
[58] Field of Search .................................... 514/313, 569, 514/738, 723

[56] References Cited

U.S. PATENT DOCUMENTS 5,420,141  5/1995  Biogegrain et al. .................... 514/314

FOREIGN PATENT DOCUMENTS

WO88/02625  4/1988  WIPO .

OTHER PUBLICATIONS

Sirenius et al, *J. Pharm. Sci.*, 66, No. 6, Jun. 1979.
Sheen et al, *J. Pharm. Sci.*, 118, No. 2, 1995 (Abstract).

*Primary Examiner*—Phyllis G. Spivack
*Attorney, Agent, or Firm*—Mark P. Bauman; Michael D. Alexander

[57] ABSTRACT

This invention provides solid pharmaceutical dispersions comprising a poorly soluble drug substance, as SR48692 or naproxen, xylitol and Transcutol, and a method of preparing such dispersions comprising the steps of dissolving the poorly soluble drug substance in Transcutol and adding the solution to xylitol. The dispersions exhibit good pharmaceutical properties and reduced levels of impurities and degradation products.

7 Claims, No Drawings

SOLID PHARMACEUTICAL DISPERSIONS

BACKGROUND OF THE INVENTION

Solid dispersions have been used to increase the dissolution rate and bioavailability of drugs that are poorly water soluble. The carriers used have been physiologically inert compounds that are readily water soluble, such as polyethylene glycols. Two techniques which have been used to prepare solid dispersions are the fusion technique and the solvent technique. In the fusion technique, drug substance is dissolved in a molten carrier and the mixture cooled to form a solid. In the solvent technique, drug substance and carrier are dissolved in a solvent, followed by removal of the solvent by evaporation or freeze drying.

The preparation of solid dispersions comprising a drug substance featuring good pharmaceutical properties is difficult. Problems which frequently occur during preparation include: degradation of drug substance at the temperature of the molten carrier; reaction of the drug with the molten carrier; and incomplete solidification of the product, e.g., the carrier remaining largely amorphous.

DESCRIPTION OF THE PRIOR ART

Sirenius et al, *J. Pharm. Sci.*, 66, No. 6, June 1979 disclose solid dispersions prepared from esters of p-aminobenzoic acid and xylitol.

SUMMARY OF THE INVENTION

We have discovered that the combination of Transcutol and xylitol provides a carrier for solid pharmaceutical dispersions which can reduce impurities and/or degradation products. The dispersion maintains a high degree of crystallinity, acceptable hygroscopicity and rapidly dissolves in water and has good bioavailability.

In accordance with the invention, there is provided a solid dispersion comprising a poorly soluble drug substance, Transcutol and xylitol.

In another embodiment of the invention, there is provided a method of preparing such dispersion comprising the steps of dissolving a poorly soluble drug substance in Transcutol and adding the solution to xylitol.

DESCRIPTION OF THE PREFERRED EMBODIMENTS

Transcutol is also known as diethyleneglycol monoethyl ether. The Transcutol is present in an amount of 0.1 to 30%, preferably 0.5 to 25% and most preferably, 1 to 20% by weight of the solid dispersion. Transcutol is commercially available and/or can be prepared by techniques well known to those skilled in the art.

Xylitol is a pentahydric alcohol derived from xylose having the structure $CH_2OH(CHOH)_3CH_2OH$ and a molecular weight of 152.1. The xylitol is present in an amount of 40 to 99.9%, preferably 45 to 99.5%, and most preferably 50 to 99% by weight of the solid dispersion. Xylitol is commercially available, and/or can be prepared by techniques well known to those skilled in the art.

The invention can be practiced with a wide variety of drug substances. The drug substance preferably is present in an essentially pure form. The drug substance may be poorly soluble and must be soluble in at least one liquid medium. By "poorly soluble" it is meant that the drug substance has a solubility in an aqueous medium of less than about 10 mg/ml, and preferably of less than about 1 mg/ml.

Suitable drug substance can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), antiallergic agents, stimulants and anoretics, sympathomimetics, thyroid agents, vasodilators and xanthines. Preferred drug substances include those intended for oral administration. A description of these classes of drugs and a listing of species within each class can be found in Martindale, the extra Pharmacopoeia, Twenty-ninth Edition, the Pharmaceutical Press, London, 1989, the disclosure of which is hereby incorporated by reference in its entirety. The drug substances are commercially available and/or can be prepared by techniques known in the art.

The drug substance is present in an amount of 0.1 to 30%, preferably 0.5 to 25% and most preferably 1 to 20% by weight of the solid dispersion.

U.S. Pat. No. 5,420,141 describes pyrazole derivatives possessing an amide group substituted at position 3, and methods for the preparation thereof. A compound which has shown clinical promise is SR48692, described therein in Example 13. SR48692 has the structure:

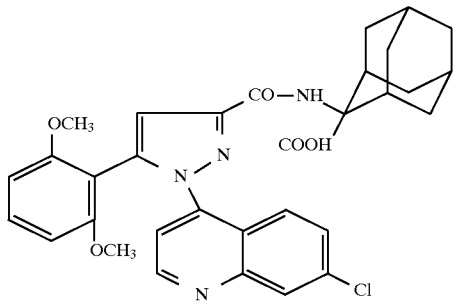

Extensive efforts have been made to formulate SR48692 into an acceptable solid dispersion. As described below, attempts to formulate this compound with conventional solid carriers such as high molecular weight polyethylene glycols did not yield satisfactory results.

The dispersions can be prepared by the steps of: dissolving the poorly soluble drug substance in Transcutol, optionally in the presence of a strong base such as NaOH or KOH, and adding the solution to xylitol to form a crystalline dispersion. The strong base is preferred when the acid form of the drug substance is employed. Up to 1 or more equivalents of base per equivalent of drug substance can be employed. In the final dispersion, the drug substance can be either in a crystalline state or amorphous depending on the drug substance selected and the drug concentration.

The following examples further illustrate the invention.

EXAMPLES 1–4

Preparation of Solid SR48692 Dispersions and Comparative Examples A–D

The formation of a solution by dissolving SR48692 in a basic solvent system was the initial step. SR48692 was dissolved in PEG 400 or Transcutol (diethyleneglycol monoethyl ether available from Gattefosse) with the addition of aqueous sodium or potassium hydroxide at approximately stoichiometric levels with SR48692. Concentrated aqueous sodium hydroxide (35% w/v) or potassium hydroxide (45% w/v) was added to a suspension of SR48692 in the organic solvent Transcutol available from Gattefosse; dissolution occurred in less than 15 minutes. Initially, preparations were formed using sodium hydroxide as the base, however, in later formulations potassium hydroxide was used. The basic solution was then added to molten PEG 8000 or xylitol at various levels to produce dispersions at final drug concentration up to approximately 9%. After addition of the SR48692 solution to the carrier, the system was mixed for approximately 2 minutes, then allowed to crystallize overnight at 20° C. Listed below are the combinations which were investigated:

| Example | Solvent | Carrier | Approx. Drug Conc. (% w/w) |
|---------|---------|---------|----------------------------|
| 1 | Transcutol/NaOH | Xylitol | 3% |
| 2 | Transcutol/NaOH | Xylitol | 5% |
| 3 | Transcutol/KOH | Xylitol | 8% |
| 4 | Transcutol/NaOH | Xylitol | 8% |
| A | Transcutol/NaOH | PEG 8K | 3% |
| B | PEG 400/NaOH | Xylitol | 5% |
| C | PEG 400/NaOH | PEG 8K | 5% |
| D | PEG 400/KOH | Xylitol | 8% |

HPLC results were obtained for measurement of potency as well as to check the impurity levels. The column used was a Nucleosil C18 with a mobile phase consisting of 0.01M potassium phosphate monobasic (pH=2.5)/acetonitrile (270/730) at a flowrate of 1.0 ml/min. Injection volume was 10 microliters and the detection method was by UV (at 230 nm). The instrument utilized throughout the study was a Hewlett Packard 1050 system. For the assay determination, the samples were first diluted in methanol/ammonium hydroxide (99.8/0.2), then further diluted in methanol to obtain a final SR48692 concentration of 0.04 mg/ml. For the impurity profile, the samples were diluted to a final SR48692 concentration of 1.0 mg/ml by the same procedure. The known impurities were quantitated versus external standards at a concentration of 0.0005 mg/ml. Any unknown impurities were quantified versus an external standard. All impurities greater than 0.01% were added to obtain the total impurity result.

Differential scanning calorimetry (DSC) scans were performed on the Perkin Elmer System-7 at 10° C./min heating rate from 25°–125° C. under nitrogen purge. Approximately 5 mg samples were encapsulated in aluminum pans. The instrument was calibrated with indium (melting point 156.6° C.) and tin (melting point 231.9° C.) prior to use.

The dissolution rate of 25 mg SR48692 solid dispersion in hard gelatin capsules were measured in deionized water (900 ml, pH=5.5, unbuffered) at 37° C. A Distek USP dissolution system (Apparatus 2) with a paddle speed of 100 RPM was used. Dissolution rate was monitored by UV (Hewlett Packard 8452A) at 234 nm. The pH was found to be relatively unchanged at the final concentrations (approximately 0.03 mg/ml).

The VTI MB300 system was used to investigate the hygroscopicity of a batch of solid dispersion with acceptable impurity levels. The system was run from 5–80% RH in 5% steps at 25° C. The samples were purged at 50° C. and about 0% RH prior to analysis.

The xylitol/Transcutol formulations containing approximately 8% drug were analyzed with the Scintag XDS system in order to determine whether the drug exists in a crystalline or a molecularly dispersed state within the dispersion. Samples were scanned at 2 degrees (2-theta)/minute and compared with pure xylitol. The system was run using Cu k-alpha radiation at 45 kv/40 ma and a liquid nitrogen cooled solid state germanium detector.

The results obtained for total impurity level and the assay for solid dispersions with PEG 8000 or xylitol as the carrier in combination with Transcutol or PEG 400 as the solvent are shown in Table 1.

TABLE 1

Summary of HPLC RESULTS

| Example | % Impurity | Assay (%) | Nominal Conc. (%) |
|---------|------------|-----------|-------------------|
| A | 28.0 | 2.1 | 3 |
| 1 | 0.74 | 2.8 | 3 |
| 2 | 0.40 | 5.2 | 5 |
| B | 1.4 | 5.1 | 5 |
| C | 4.5 | 4.8 | 5 |
| 3 | 0.55 | 9.4 | 8 |
| D | 19.2 | 6.6 | 8 |
| 3 | 0.42 | 8.6 | 8 |
| 3 | 0.36 | 8.8 | 8 |

The total batch size for these samples was about 10 g. At approximately 3% drug concentration, the use of PEG 8000 with Transcutol resulted in gross degradation as reflected in the high total impurity level and the lower assay value (Example A). In contrast, the combination of xylitol with Transcutol produced a formulation with a significantly lower total impurity level of 0.74% (Example 1).

At approximately 5% drug concentration, the combination of xylitol as the carrier with Transcutol as the solvent again produced an acceptable impurity level of 0.40% (Example 2). The total impurity levels for the xylitol/PEG 400 (Example B) and the PEG 8000/PEG 400 (Example C) were 1.4% and 4.5% respectively, both unacceptable levels. It appeared that the use of PEG 8000 as the carrier or PEG 400 as the solvent resulted in high impurity levels. The carrier/solvent combination of xylitol/Transcutol demonstrated unexpectedly lower impurity levels compared to xylitol/PEG.

At high drug concentrations (approximately 8–9%), the use of potassium hydroxide versus sodium hydroxide was shown to result in equally low levels of impurity (Example 3). The average impurity level for three 10 gram batches with KOH were 0.44±0.10%. As was observed previously, the use of PEG 400 as the solvent resulted in unacceptable degradation (19.2% total impurity, Example D).

HPLC data for two batches of approximately 100 g made with xylitol as the carrier, Transcutol as the solvent and either potassium or sodium hydroxide as the base exhibited low impurity levels; 0.30% (Example 3) and 0.27% (Example 4) total impurities were observed for the KOH and NaOH based systems, respectively.

Differential scanning calorimetry (DSC) scans obtained at 10° C./min for the batches evidenced that the effect of the formulation components on the melting behavior of xylitol is surprisingly low. The melting peak of the KOH based formulation (Example 3) was 89.4° C., a depression of 8.7 degrees. Similarly, the melting peak of the NaOH formulation (Example 4) was 96.3° C., a depression of only 1.8 degrees. X-ray powder diffraction patterns of the formulation indicated a predominantly crystalline xylitol phase.

A screening dissolution test was run in USP Apparatus 2 with water at pH 5.5 (unbuffered) at 37° C. comparing the solid dispersion of this invention (Example 2) with unformulated (jet-milled) SR48692. The solid dispersions provide enormous dissolution enhancement with respect to pure drug and low impurity levels (0.4%). The fraction dissolved was well over 90% in 10 minutes; in contrast, the capsules containing SR48692 drug substance (unformulated) did not reach 10% dissolved at the end of the experiment of 60 minutes. Dissolution experiments incorporating the solid dispersion at 25 mg/capsule (example 2) at pH 7.0 (37° C.) with 0.5% sodium lauryl sulfate as the dissolution medium also showed rapid dissolution, with more than 90% dissolved after 10 minutes.

The hygroscopicity of a solid dispersion based formulation (Example 3) was screened by running a sample at 25° C. from 5–80% RH in 5% steps. The data showed relatively low (~1%) moisture uptake at 25° C. below 60% RH; this level would be acceptable for a solid formulation. Hysteresis data showed the moisture uptake at 80% RH was reversible; as the RH was decreased back down to 5%, the moisture was not retained.

The x-ray powder diffraction patterns of the xylitol/Transcutol formulations (Examples 3–4) compared with pure xylitol suggest that the dispersion appears to be a "crystalline" dispersion rather than an amorphous dispersion/solid solution. This hypothesis was confirmed by hot-stage microscopy. It appears that the xylitol/Transcutol/base formulation has high dissolution rates despite the existence of the drug in a crystalline state. The explanation for this observation is that the crystalline state is likely the salt form rather than the acid form.

The formulation of solid dispersions at dosages up to 40 mg/capsule containing xylitol/Transcutol/NaOH (or KOH) were shown to have acceptable impurity levels (typically<0.5%) and rapid dissolution (>90% in 10 minutes) in water at 37° C. (pH=5.5). Analysis by differential scanning calorimetry and x-ray powder diffraction indicated the existence of crystalline xylitol and crystalline drug. The crystalline nature of the drug was confirmed by observation of the formulation with polarized light microscopy at the melting temperature of xylitol. FTIR analysis of the solid produced when adding the solid dispersion formulation to 0.1N HCl indicated a desirable amorphous acid phase. This suggests that the solid dispersion could have similar bioavailability when compared to the liquid. Advantages of the dispersion formulation include improved manufacturability and ease of fill into hard gel capsules.

Naproxen

The formulation of naproxyn was prepared by dissolving 4.6 g of naproxyn in 4.6 g of Transcutol (diethylene glycol monoethyl ether) with the addition of 2 g of 45% w/v aqueous potassium hydroxide. The naproxyn dissolved within a few minutes of adding the basic solution. The naproxyn solution was then added to molten xylitol at 100° C. at a ratio of approximately 1:3 by weight. The product was mixed for several minutes, then poured into a crystallizing dish at room temperature. After 24 hours, the product was removed and ground in a mortar and pestle. The final naproxyn concentration was approximately 10% by weight. The product was a white crystalline powder with a melting point of approximately 90° C.

The dissolution rate using USP Apparatus 2 of the naproxyn solid dispersion formulation (filled into size 0 hard gelatin capsules) was compared with pure naproxyn and the potassium salt of naproxyn under the following conditions:

Dissolution media—0.01M phosphate buffer, pH=6
Volume—1000 ml
RPM—50
Dosage—50 mg active for formulation, naproxyn and naproxyn potassium salt
Temperature—37° C.

The dissolution results (3 capsules/formulation) are summarized below:

| Formulation | % Dissolved at 30 minutes |
| --- | --- |
| Xylitol Dispersion of Naproxyn Potassium | 97.4 +/− 0.8 |
| Naproxyn | 57.1 +/− 18.5 |
| Naproxyn Potassium | 98.3 +/− 1.0 |

The formulation in the capsules containing the xylitol dispersions dissolved faster than the capsules containing naproxyn drug substance. The formulation in the capsules containing the potassium salt of naproxyn dissolved in a similar manner to the xylitol based formulation.

The advantage of the xylitol/Transcutol/base dispersion versus a formulation containing the acid form of a drug is to cause partial or complete conversion to the salt which will, in general, enhance dissolution rate and solubility. The advantage of the xylitol dispersion versus a formulation containing the salt form is to avoid the potential problems involved with storage of salts (e.g., hygroscopicity). There are several advantages of using xylitol specifically as a carrier. It crystallizes well despite the inclusion of 20% or more drug and Transcutol. The melting point (95° C.) is higher than polyethylene glycols (50°–60° C.) and there appears to be little melting point depression for xylitol dispersions. In addition, it is highly water soluble, resulting in rapid dissolution and drug release.

Having described the invention with reference to its preferred embodiments, it is to be understood that modifications within the scope of the invention will be apparent to those skilled in the art.

We claim:

1. A solid dispersion comprising:
   a) a poorly soluble drug substance selected from the group consisting of SR48692 and naproxyn:
   b) xylitol and
   c) Transcutol.

2. The solid dispersion of claim 1 wherein said drug substance is SR48692.

3. The solid dispersion of claim 1 wherein said drug substance is naproxyn.

4. The solid dispersion of claim 1 further comprising a base.

5. The solid dispersion of claim 2 further comprising a base.

6. The solid dispersion of claim 3 further comprising a base.

7. A method of preparing a dispersion comprising the steps of:
   a) dissolving a poorly soluble drug substance selected from the group consisting of SR48692 and naproxyn in Transcutol;
   b) adding the solution to xylitol.

* * * * *